United States Patent [19]

Ellinger et al.

[11] 4,083,637
[45] Apr. 11, 1978

[54] INSPECTION APPARATUS FOR CONTAINERS WITH TRANSPARENT BOTTOMS

[75] Inventors: Bernd Ellinger; Konrad Holler, both of Regensburg, Germany

[73] Assignee: Hermann Kronseder, Regensburg, Germany

[21] Appl. No.: 731,062

[22] Filed: Oct. 8, 1976

[30] Foreign Application Priority Data

Oct. 11, 1975 Germany .............................. 2545678

[51] Int. Cl.² ............................................ G01N 21/32
[52] U.S. Cl. ................................. 356/240; 250/223 B
[58] Field of Search .................... 356/240; 250/223 B; 209/111.7 T

[56] References Cited

U.S. PATENT DOCUMENTS

| | | | |
|---|---|---|---|
| 3,191,773 | 6/1965 | Wyman | 356/240 UX |
| 3,292,785 | 12/1966 | Calhoun | 356/240 X |
| 3,415,370 | 12/1968 | Husome | 356/240 X |

Primary Examiner—John K. Corbin
Assistant Examiner—Matthew W. Koren
Attorney, Agent, or Firm—Joseph P. House, Jr.

[57] ABSTRACT

Inspection equipment for detection of foreign matter particles in the bottom area of containers with transparent bottoms, such as glass bottles. The equipment has a driven rotor the front face of which lies in the image plane of a projection optic with the illuminated bottle bottom serving as the object plane. The rotor has a first optical element in the form of a radially extending mirror which focuses the incident radiation on a fixed position photoelectric element. The output signal of the photoelectric element feeds an evaluator which responds to a certain decrease of the incident light intensity. The rotor is provided with a second optical element which is responsive to radiation from the center of the container bottom and which signals a second photoelectric cell, which feeds a second evaluator. Both evaluators signal container reject mechanism.

10 Claims, 7 Drawing Figures

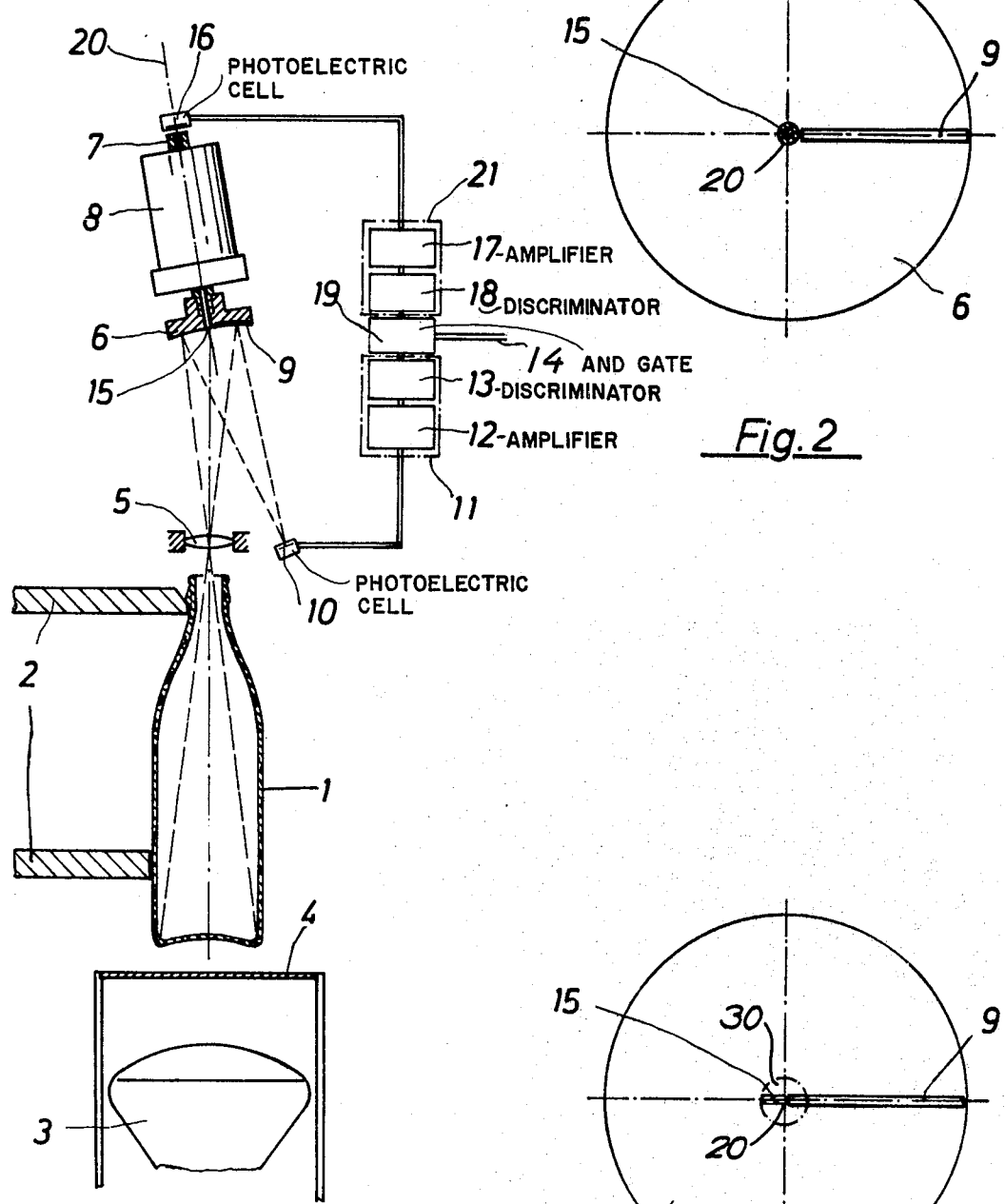

INSPECTION APPARATUS FOR CONTAINERS WITH TRANSPARENT BOTTOMS

BACKGROUND OF THE INVENTION

A test setup of this kind is already known, where the scanning of the bottle bottom for foreign matter particles is done entirely by the mirror element radially outward from the axis of the front face of the rotor, which, upon a complete revolution of the rotor, scans the entire bottom of the bottle. This known method of inspection generally yields good results. Small particles, however, located exactly in the central area of the bottom of the bottle are not always detected. They are only partially discerned by the concave mirror element and the change in light quantity or intensity impinging upon the photocell during one revolution of the mirror segment is correspondingly small.

SUMMARY OF THE INVENTION

The invention has the object to improve test apparatus of the kind described above with simple means in such a way that small particles located exactly at the center of the glass bottom can be detected with great reliability.

According to the invention, this objective is reached by providing within the zone of the axis of rotation of the rotor face a second optical element which accepts the light coming from the central area of the glass bottom and sends it to a second fixed position photoelectric cell. The second photoelectric cell feeds an evaluator which triggers a container reject mechanism. In preferred embodiments, the radial dimension of the field of inspection scanned by the radial segment concave mirror (the first optical element) is several times larger than the inspection field scanned by the second optical element.

The invention is based in part on the idea to split the bottle bottom into two different zones of inspection, i.e., the relatively small circular central zone and the significantly larger adjacent outer ring zone and to coordinate with both inspection zones individual test units comprising optical element, photosensor and discriminator, or equivalent, for each of them.

The two test units may be adapted to their specific purposes without compromise. For the second optical element an effective area of only a few square mm suffices, such that even very small foreign matter particles at the center of the bottle bottom lead to strong or complete darkening of the corresponding photoelectric component. The outer large rim zone is scanned with well-known reliability by the rotating mirror segment and its companion photoelectric sensor.

Various embodiments of the invention utilize different types and dispositions of the second optical element. It may take a circular form or may take a stripe-shaped form. It may be placed on or concentrically with the axis of rotation of the rotor front face or be displaced in relation to it. The second optical element may comprise a concave mirror or a fiber optics guide which transmits light to a location remote from its pickup point.

Utilization of a fiber optics guide has certain advantages. It facilitates a construction of utmost simplicity. Preferably, the fiber optics guide is placed inside a rotor bore which is on the axis of rotation of the rotor and inside the shaft of the rotor with the second photocell located near that shaft end remote from the front rotor face carrying the optical elements.

Utilization of a concave mirror offers certain advantages. The concave mirror makes it possible to arrange both light sensors (the photoelectric cells) in close proximity on a common base plate. One of the two photocells is ringshaped and placed concentrically with the other one. The coordination of the photocells depends upon the configuration of the two concave mirrors.

Other objects, features and advantages of the invention will appear from the disclosure hereof.

DESCRIPTION OF THE DRAWINGS

FIG. 1 is a schematic view, partly in side elevation and partly in vertical section, for beverage bottles with a fiber optics guide as the second optical element.

FIG. 2 is a plan view of the face of the rotor of the embodiment of FIG. 1.

FIG. 3 is a plan view of a modified embodiment of the rotor of FIGS. 1 and 2.

DESCRIPTION OF THE PREFERRED EMBODIMENTS

Figure 4:
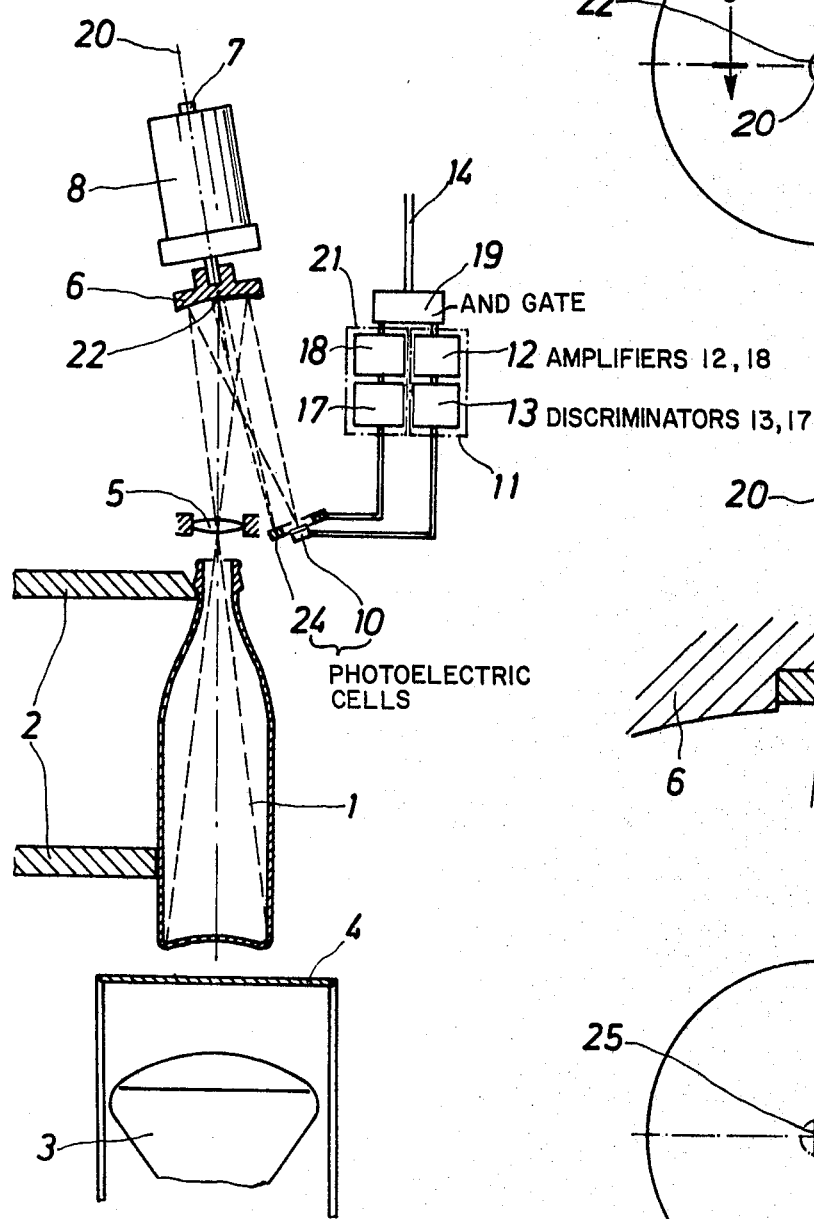
FIG. 4 is a schematic view, partly in side elevation and partly in vertical section of a modified embodiment of the invention utilizing a concave mirror as the second optical element.

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

The inspection apparatus according to FIGS. 1 and 2 is designed for the checking for contaminating particles of empty containers having transparent bottoms, such as beverage bottles 1. This apparatus is typically one part of an automatic bottle inspection machine not specifically shown here. The bottles to be tested are moved by a star wheel 2 over a light source 3 which is covered by a diffusing glass plate 4. The bottom of the bottle is thus illuminated diffusely. A lens 5 in a fixed position above the mouth of the bottle projects an image of the illuminated bottle bottom onto the downwardly directed face of a rotor 6 which is fastened to shaft 7 of a motor 8. Motor 8 rotates the rotor 6. The face of the rotor 6, which is otherwise non-light reflective, carries a narrow, radially extending concave mirror segment 9 which focuses and reflects the light from whatever image section of the bottle bottom might be scanned at that moment on a fixed-position first photosensor such as photoelectric cell 10. For this purpose, the axis of rotation 20 of the rotor 6 and motor 8 are slightly tilted with respect to the axis of the bottle 1 and the optical axis of lens 5.

If during rotation of the concave mirror segment 9 a region of the glass bottom is scanned which contains a foreign matter particle, the reflected light intensity falls off temporarily and the output voltage of the photocell 10 drops accordingly. This signal is fed into an evaluation stage 11 of an electronic circuit. The evaluator 11 includes amplifier 12 and a discriminator 13 and produces an output signal which actuates over control line 14 a throwout mechanism (not shown) for the contaminated bottle.

In the embodiment of FIG. 1, the rotor 6 and the shaft 7 affixed to it are provided with a through-hole or bore on the axis of rotation 20. Within this bore, which may have a diameter of 4 mm, is disposed a light pipe or fiber optics guide 15 of conventional construction. The light transmitting end of the guide 15 terminates flush at the upper end of shaft 7. The light receiving end of guide 15 terminates flush on the front face of rotor 6. The light guide 15 accepts the light coming from a circular central area of the glass bottom and conducts it on to a second fixed-position optical element, such as photoelectric cell 16, which is juxtapositioned and closely spaced with respect to the upper end of shaft 7. The output voltage of photocell 16 thus depends upon the light radiating out from the center of the glass bottom only. The second photocell 16 is also connected to a second evaluator 21, an amplifier 17 and discriminator 18. The outputs of both evaluators 11 and 21 are connected over an AND-gate 19 with the control line 14 in such a way that by darkening of one photocell by foreign matter within the area of the bottle bottom, a throwout impulse is sent out independently of the state of the other photocell.

In the design according to FIGS. 1 and 2, the front face of light guide 15 lies within the front face of rotor 6 and is shaped circularly and is positioned on rotation axis 20. However, the light receiving end of the light guide 15 may be flattened and extend radially with respect to the axis of rotation 20 as shown in FIG. 3. Accordingly, the nearly rectangular or strip-shaped face of the light guide 15 is disposed eccentric to the axis 20 and will sweep a circular area of inspection for a revolution of rotor 6, as shown by the zone enclosed by the dash-dotted circle line 30 in FIG. 3. This arrangement improves the sensitivity of the second optical element 15 to variations in light intensity sensed thereby. As shown in FIG. 3, there is an overlap of the inspection area of light guide 15 and that of concave mirror element 9.

Figure 5:
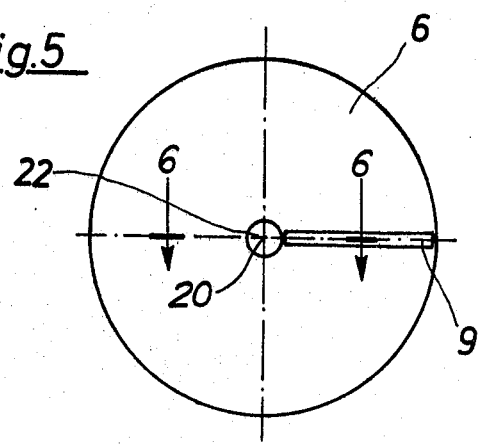
FIG. 5 is a plan view of the front face of the rotor of the embodiment of FIG. 4.
Figure 6:
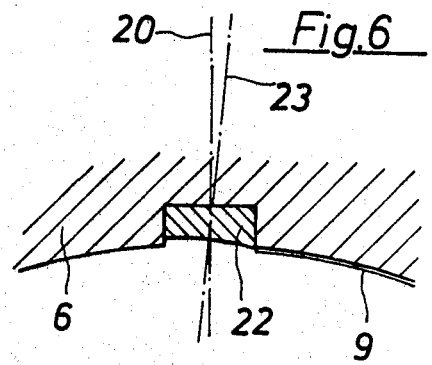
FIG. 6 is a fragmentary enlarged cross section along the line 6—6 of FIG. 5.

The test apparatus embodiment of FIGS. 4—6 corresponds to that according to FIGS. 1 and 2 with the exception of the design of the second optical element and the second photocell. Here the second optical element comprises a circular concave mirror 22, which may by way of example have a diameter of 5 mm. Mirror 22 is placed concentrically with the rotation axis 20 and is recessed into the front face of rotor 6.

Figure 7:
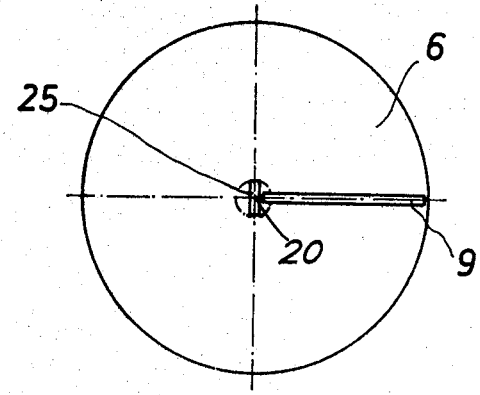
FIG. 7 is a plan view of a slightly modified version of the rotor in accordance with the embodiment of FIGS. 5 and 6.

As can be seen from FIG. 6, the optical axis 23 of the concave mirror 22 is slightly tilted with respect to the rotational axis 20 of the rotor 6 and the optical axis of the concave mirror segment 9. Tilt and curvature of the concave mirror 22 are chosen in such a way as to focus the incident radiation on a ring-shaped second photocell as the rotor turns. The second photocell 24 is arranged concentrically with the first photocell 10 and is connected to amplifier 17 of the evaluating unit 21. Instead of a full concave mirror 22, a stripe-shaped concave mirror element 25 may be used, as shown in FIG. 7. The concave mirror segment 25 represents a fraction of the concave mirror according to FIGS. 5 and 6 and increases the sensitivity thereof and also focuses the incident radiation on the ring-shaped photocell 24. An eccentric positioning of the concave mirror element 25 similar to the eccentric arrangement of the light guide 15 of FIG. 3 is also possible.

What is claimed is:

1. In test apparatus for the detection of foreign matter particles in the bottom area of containers having transparent bottoms and including a driven rotor having a front face lying in the image plane of a projected image of the illuminated container bottom, a first photoelectric cell, said face being provided with a first optical element which scans radiation projected from said bottom and transmits the incident radiation to a first photoelectric cell, said apparatus having an evaluator for the output signals of the photoelectric cell which upon a certain decrease of the incident light due to the presence of foreign matter delivers a signal, the improvement in which a second optical element is disposed in said image plane in the region of the axis of rotation of said rotor and is rotatable therewith and which receives radiation emitted from the central area of the container buttom, a second photoelectric cell to which said second optical element transmits said radiation, and an evaluator which emits a signal upon a certain decrease of the radiation transmitted by the second optical element due to the presence of foreign matter in said central area.

2. Test apparatus of claim 1 in which the first optical element comprises a segment of a concave mirror disposed radially over said face.

3. Test apparatus of claim 1 in which the extent of the inspection field scanned by the first optical element exceeds the inspection field of the second optical element.

4. Test apparatus according to claim 1 in which the effective area of the second optical element is shaped circularly and arranged concentrically to the rotation axis of the rotor front face.

5. Test apparatus according to claim 1 in which the effective area of the second optical element is stripe-shaped and is arranged radially with respect to the axis of rotation of the rotor face.

6. Test apparatus of claim 5 in which the first optical element comprises a radially extending reflective segment and the second stripe-shaped optical element is disposed at substantially a right angle to the first optical element.

7. Test apparatus according to claim 1 in which the second optical element comprises a fiber optics guide having a light receiving end at the center of the rotor and a light transmitting end adjacent said second photoelectric cell.

8. Test apparatus according to claim 7 in which the rotor has an axial bore, said fiber optics guide being disposed within said bore, said second photoelectric cell being disposed on the axis of rotation of said rotor.

9. Test apparatus according to claim 1 in which said second optical element comprises a concave mirror which focuses the incident radiation on the second photoelectric cell.

10. Apparatus for the detection of foreign matter particles in the bottom of containers having transparent bottoms, comprising:
   a driven rotor having a front face lying in the image plane of a projected image of an irradiated container bottom.
   one photoelectric cell and another photoelectric cell comprising an annular photosensitive ring surrounding the one cell,
   a radial segment of a concave mirror and another concave mirror disposed on said front face of said rotor for reflecting areas of the projected radiation image including its central area and areas surrounding said central area, the optical axis of said concave mirror segment coinciding with the rotational axis of said rotor for focusing a radiation image of an area onto said one photocell and the optical axis of the other concave mirror being tilted with respect to said axis for focusing a radiation image of another area onto said other photocell, and means responsive to radiation intensity variations on said photoelectric cells due to the presence of foreign matter in said areas by producing signals indicative of said variations.

* * * * *